US00PP37810P2

(12) United States Plant Patent
Morgan

(10) Patent No.: US PP37,810 P2
(45) Date of Patent: Oct. 20, 2026

(54) ***LIMONIUM* PLANT NAMED '08LPS9'**

(50) Latin Name: ***Limonium* hybrid**
Varietal Denomination: 08LPS9

(71) Applicant: FlowerZone International Ltd, Auckland (NZ)

(72) Inventor: Edmund Morgan, Auckland (NZ)

(73) Assignee: FLOWERZONE INTERNATIONAL LTD, Auckland (NZ)

( * ) Notice: Subject to any disclaimer, the term of this patent is extended or adjusted under 35 U.S.C. 154(b) by 0 days.

(21) Appl. No.: 19/643,908

(22) Filed: Apr. 10, 2026

(51) Int. Cl.
*A01H 6/00* (2018.01)
*A01H 5/02* (2018.01)

(52) U.S. Cl.
USPC ..... Plt./358

(58) Field of Classification Search
USPC ..... Plt./358
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Limonium* plant named '08LPS9' that is characterized by its reliable perennial habit in New Zealand., its flowers with sepals that are silvery pink in color with dark pink tones developing at the base in cooler months, its consistent and repeated flower stem production throughout the summer and autumn seasons, its flowering stems that are 55 cm to 65 cm in length, its tolerance to powdery mildew, and its sturdy and robust stems.

3 Drawing Sheets

Botanical classification: *Limonium* hybrid.
Cultivar designation: '08LPS9'.

BACKGROUND OF THE INVENTION

The present invention relates to a new and distinct cultivar of *Limonium*, botanically of hybrid origin and known as a *Limonium* '08LPS9' and hereinafter referred to by its cultivar name '08LPS9'. '08LPS9' is a new cultivar of statice, a perennial grown for use in containers and cut flower production.

The new cultivar arose from an ongoing breeding program by the Inventor in Palmerston North, New Zealand with the goal of using embryo rescue techniques to create new and unique cultivars of interspecific *Limonium*. The new cultivar resulted from embryo rescue of seeds of an unpatented proprietary *Limonium* plant of hybrid origin as the female parent, designated breeder code PsPs1, in Palmerston North, New Zealand in spring of 2008. The female parent had been hand pollinated from various unpatented proprietary plants of *Limonium perezii* from the Inventor's breeding program in spring of 2008. The seeds had been pooled from the crosses and therefore the male parent of '08LPS9' is unknown. '08LPS9' was selected as a single unique plant from the crosses in spring of 2010.

Asexual propagation of the new cultivar was first accomplished under the direction of the Inventor by tissue culture initiated from meristem tissue in summer of 2010 in Palmerston North, New Zealand. Asexual propagation of the new cultivar by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish '08LPS9' as a new and unique cultivar of *Limonium*.

1. '08LPS9' exhibits a reliable perennial habit in New Zealand.
2. '08LPS9' exhibits flowers with sepals that are silvery pink in color with dark pink tones developing at the base in cooler months.
3. '08LPS9' exhibits consistent and repeated flower stem production throughout the summer and autumn seasons.
4. '08LPS9' exhibits flowering stems that are 55 cm to 65 cm in length.
5. '08LPS9' exhibits tolerance to powdery mildew.

The female parent differs from '08LPS9' in having a different shade of white flowers, a different leaf shape, and different flower stem branching. '08LPS9' can be most closely compared to *Limonium perezii* 'Purple Parachute' (not patented) and *Limonium latifolium* 'Misty Blue' (not patented). 'Purple Parachute' differs from '08LPS9' in having shorter flowering stems, flowers with sepals that are purple in color, and leaves that are wider and shorter. 'Misty Blue' differs from '08LPS9' in having flowers with smaller calyces that are lavender in color, and flowering stems that are more finely branched and airy.

'08LPS9' can also be compared to the co-pending cultivars of *Limonium* '04LPS2007', '08LPS8', and '08LPS14'. '04LPS2007' differs from '08LPS9' in having flowers with sepals that are pastel blue lavender in color. '08LPS8' differs from '08LPS9' in having flowers with sepals that are medium to dark blue in color. '08LPS14' differs from '08LPS9' in having flowers with sepals that are dark lavender in color.

BRIEF DESCRIPTION OF THE DRAWINGS

The accompanying color photographs illustrate the overall appearance and distinct characteristics of the new *Limo-*

*nium*. The photograph was taken of a plant 4 months in age as grown outdoors in a 19-cm container in Heerhugowaard, The Netherlands.

Figure 1:
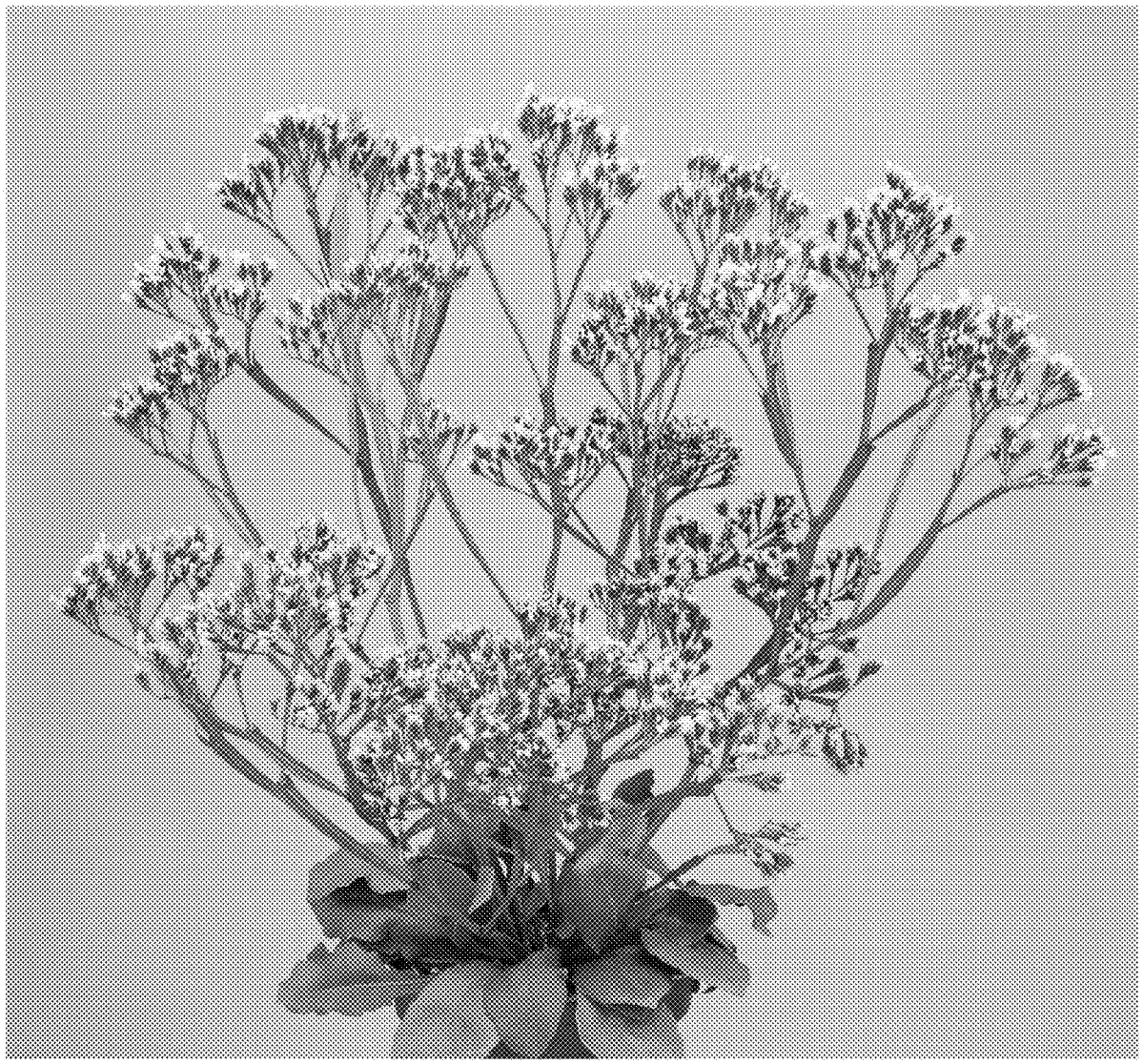

The photograph in FIG. 1 provides a side view of the plant of '08LPS9' in bloom.

Figure 2:
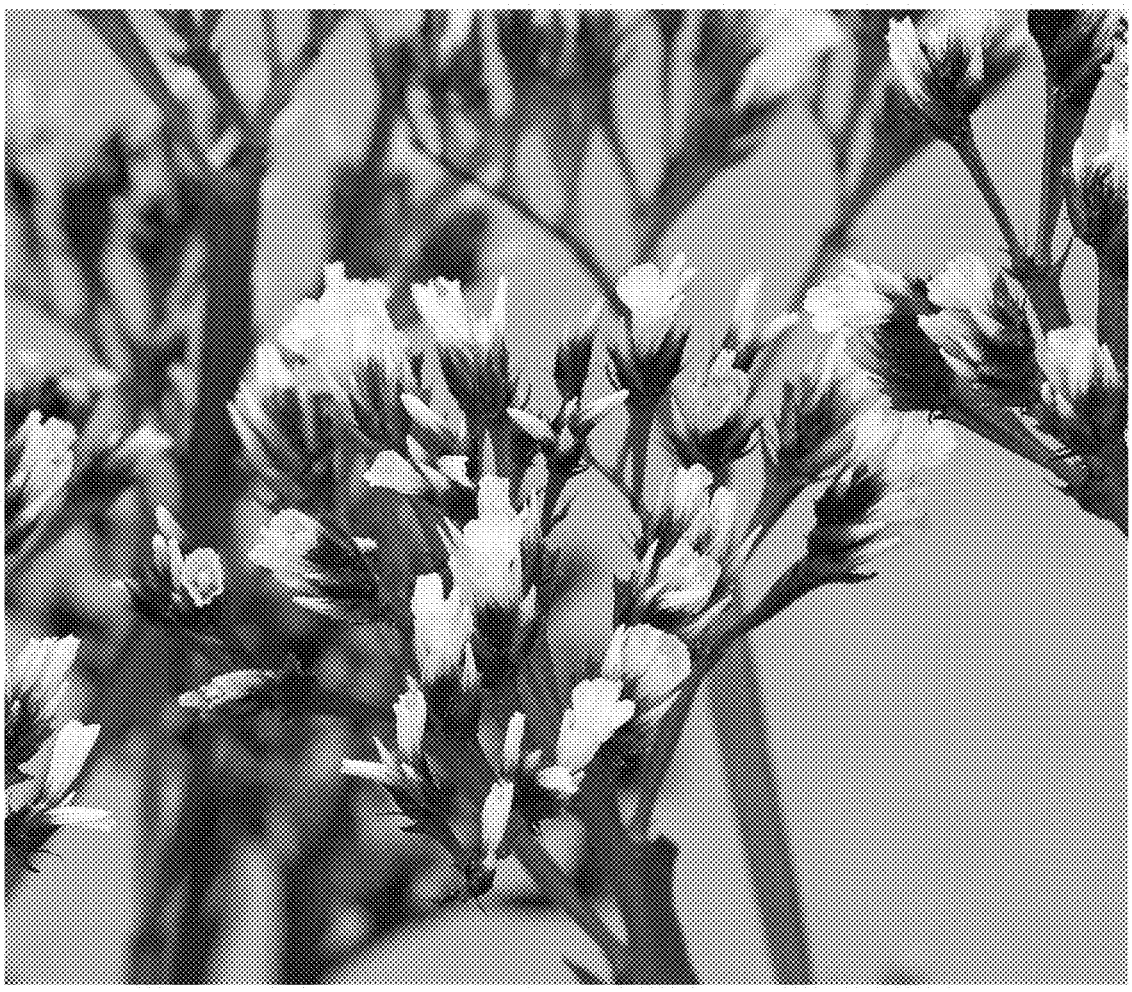

The photograph in FIG. 2 provides a close up of an inflorescences of '08LPS9'.

Figure 3:
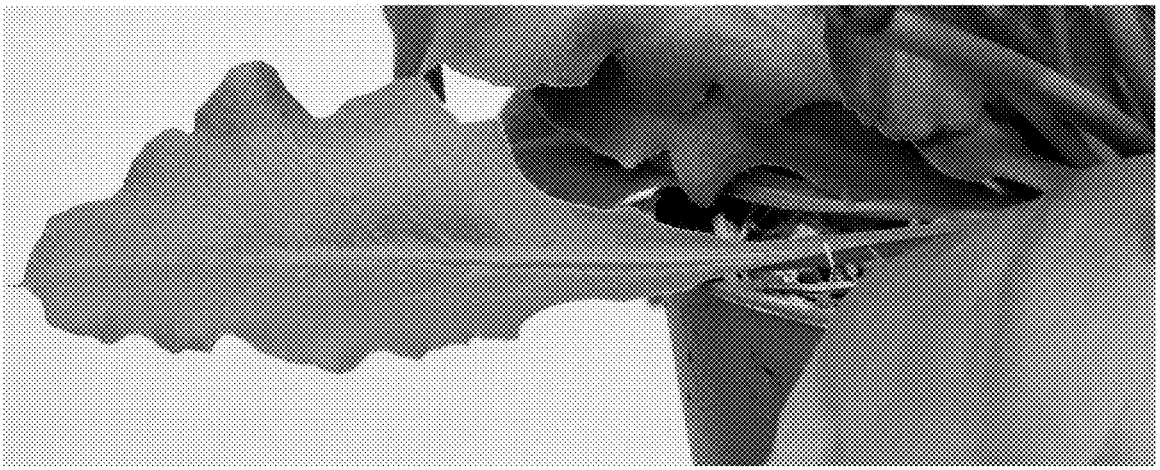

The photograph in FIG. 3 provides a close up of the foliage of '08LPS9'.

The colors in the photograph are as close as possible with the digital photography techniques available, the color values cited in the detailed botanical description accurately describe the colors of the new *Limonium*.

DETAILED BOTANICAL DESCRIPTION OF THE PLANT

The following is a detailed description of 4-month-old plants of the new cultivar as grown outdoors in 19-cm containers in Heerhugowaard, The Netherlands. The phenotype of the new cultivar may vary with variations in environmental, climatic, and cultural conditions, as it has not been tested under all possible environmental conditions. The color determination is in accordance with the 2019 (reprint of 2015 6th edition) of The Colour Chart of The Royal Horticultural Society, London, England, except where general color terms of ordinary dictionary significance are used.

General description:

*Blooming period*.—Flowering commences in 6 to 8 weeks from a planted plug, flowering continues into autumn on new flowering stems, flowering can be extended if greenhouse grown.

*Plant type*.—Herbaceous perennial.

*Plant habit*.—Upright and broadly spreading.

*Height and spread*.—13.9 cm in height (soil level to top of foliar plane), 49.3 cm in height (soil level to top of floral plane), 55.1 cm in spread as grown in a 19-cm container, stems typically reach 55 to 65 cm in length in cut flower production fields.

*Hardiness*.—At least in U.S.D.A. Zones 8 to 11.

*Diseases and pests*.—Tolerance to powdery mildew caused by *Erysiphe polygoni* has been observed, no susceptibility or resistance to pests has been observed.

*Environmental stresses*.—Drought resistant.

*Root description*.—Fibrous roots on woody rootstalks.

*Propagation*.—Tissue culture.

*Root development*.—Plugs establish in 4 weeks from stage 3 tissue culture plantlets.

*Growth rate*.—Moderate to high.

Branch description (peduncle, flowering stem):

*Branch shape*.—Flattened, wings; 2 or 3, 2.5 mm in width, entire margins, NN137C.

*Branch color*.—137B to 137C, upper surface 137A.

*Branch size*.—41.8 cm in length, 3.5 mm in diameter.

*Branch strength*.—Strong.

*Branch aspect (from soil level)*.—Main; 55° (varying between 20° and 70°), secondary; 37.5° (varying between 25° and 50°).

*Branch surface*.—Slightly glossy, smooth, glabrous.

*Branch number*.—Average of 11.

*Branching habit*.—Sturdy and robust flowering stems emerge from basal rosettes.

Foliage description:

*Leaf shape*.—Obovate.

*Leaf division*.—Simple.

*Leaf base*.—Acuminate.

*Leaf apex*.—Abruptly acute with mucronate tip.

*Leaf venation*.—Pinnate, upper surface 146D, fading towards the tip; NN137A, lower surface 146B, fading towards the tip; darker than NN137A.

*Leaf margins*.—Irregular angulate, slightly coarsely undulate, moderately covered in very short hairs, average length 0.5 mm, color is not measurable.

*Leaf attachment*.—Petiolate.

*Leaf arrangement*.—Alternate in basal rosettes.

*Leaf surface*.—Both surfaces smooth and glabrous, covered with a thin waxy layer 190A to 190B in color.

*Leaf color*.—Young upper surface; a blend of 137B and NN137D, main vein 144A, mucronate tip 185B, young lower surface; NN137C, main vein 144A, mucronate tip 185B, mature upper surface; 147A, mucronate tip greyed-purple; 185B, mature lower surface; a blend of NN137D and 191A, mucronate tip 185B.

*Leaf size*.—12.4 cm in length and 5.5 cm in width.

*Leaf aspect*.—Flat to slightly carinate.

*Leaf quantity*.—43 per basal rosette.

*Petioles*.—3.1 cm in length, 3 mm in diameter, both surfaces slightly glossy, strong, color; upper surface 146D, lower surface 146B, winged, width of wings 1 mm, 147A in color.

*Stipules*.—Stipule-like scales, 8 mm in length, 3 mm in width, upper surface 182A, thin margin 186D, lower surface 184A, thin margin 185B.

Flower description:

*Inflorescence type*.—Numerous small bell-shaped flowers arranged on compound corymbs on peduncles emerging from a basal rosette.

*Inflorescence size*.—31.2 cm in height, 31.5 cm in diameter.

*Inflorescence number*.—An average of 5 per stem.

*Flower fragrance*.—None.

*Flower quantity*.—160 flowers per inflorescence, 600 per plant, 8,500 flowers and flower buds per plant.

*Flower Lastingness*.—On plant; 10 weeks, persistent, as a cut flower; 2 to 3 weeks.

*Flower buds*.—Lanceolate in shape, 7 mm in length, 2 mm in diameter, color; NN155D, base N144D, bracts 59C, smooth, glabrous and very slightly glossy.

*Flower type*.—Rotate, single, consisting of one whorl of petals and one whorl of sepals.

*Flower aspect*.—Upright to very slightly outward.

*Flower size*.—Average of 1.5 cm in height, 5 mm in diameter.

*Sepals*.—Average of 5, average of 1 cm in length, tubular in shape, no margins present, sepals fused into upper portion campanulate, broad obtuse apex, both surfaces smooth, glabrous, slightly glossy and slightly papery, color; upper and lower surface when opening; upper (campanulate) part slightly transparent NN155D, veined 185D, lower (tubular) part 144B, veined 185B, upper and lower surface fully open; upper (campanulate) part slightly transparent NN155D, veined 177C and 177D, lower (tubular) part 144B, tinged 185C and 185D, veined 185B.

*Petals.*—5, rotate in arrangement, 1 whorl, 1.3 cm in length, 2.5 mm in width, narrowly spathulate in shape, retuse base, entire margins, both surfaces smooth, glabrous and slightly glossy, color; when opening and fully open upper and lower surface; a blend of 4D and 157C, lower 70% (narrow part of petal) NN155D.

*Floral bracts.*—At the base of each calyx a single bract is placed, oblong in shape, apex acute, base cuneate, 7 mm in length, 2 mm in width, surfaces are smooth and glabrous and slightly glossy, entire margins, color; both surfaces 146A, tips 61A.

*Pedicels.*—None, individual flowers sessile to secondary peduncles.

*Calyx.*—Rotate, 1 cm in length, 4 mm in diameter.

Reproductive organs:

*Gynoecium.*—Pistils; 5, 8 mm in length, stigma; pointed in shape, NN155D in color, style; an average of 7.7 mm in length, N155A in color, ovary; 146A in color.

*Androecium.*—Stamens; 5, anthers; dorsifixed, oblong in shape, 1 mm in length, 0.4 mm in width, color; 4B, filaments; 8 mm in length and NN155D in color, pollen; low in quantity and 4C in color.

*Fruit and seed.*—No fruit or seeds have been observed to date.

It is claimed:

1. A new and distinct cultivar of *Limonium* plant named '08LPS9' as herein illustrated and described.

* * * * *